(12) United States Patent
Alzaidi

(10) Patent No.: US 9,151,722 B2
(45) Date of Patent: Oct. 6, 2015

(54) SYSTEMS FOR DETERMINING AND IMAGING WAX DEPOSITION AND SIMULTANEOUS CORROSION AND WAX DEPOSIT DETERMINATION IN PIPELINES

(71) Applicant: KING ABDULAZIZ UNIVERSITY, Jeddah (SA)

(72) Inventor: Samir Abdul-Majid Alzaidi, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 14/497,304

(22) Filed: Sep. 25, 2014

(65) Prior Publication Data

US 2015/0198544 A1    Jul. 16, 2015

Related U.S. Application Data

(60) Provisional application No. 61/927,950, filed on Jan. 15, 2014.

(51) Int. Cl.
| | | |
|---|---|---|
| *G01N 23/204* | (2006.01) | |
| *G01N 17/04* | (2006.01) | |
| *G01N 23/00* | (2006.01) | |
| *G01T 1/24* | (2006.01) | |
| *G01T 3/08* | (2006.01) | |

(52) U.S. Cl.
CPC .............. *G01N 23/204* (2013.01); *G01N 17/04* (2013.01); *G01N 23/005* (2013.01); *G01T 1/24* (2013.01); *G01T 3/08* (2013.01)

(58) Field of Classification Search
CPC .................................................. G01N 23/005
See application file for complete search history.

(56) References Cited

U.S. PATENT DOCUMENTS

| | | | |
|---|---|---|---|
| 3,247,384 A | * | 4/1966 | Brady ....................... 250/496.1 |
| 4,580,053 A | | 4/1986 | Snyder |
| 5,195,117 A | | 3/1993 | Ong |

(Continued)

FOREIGN PATENT DOCUMENTS

| | | | | |
|---|---|---|---|---|
| JP | 58-063878 | A | * | 4/1983 |
| JP | 61-204510 | A | * | 9/1986 |

(Continued)

OTHER PUBLICATIONS

Abdul-Majid et al. "Asphalt and paraffin scale deposit measurement by neutron back diffsusion using 252Cf and 241Am-Be sources", Middle East Nondestructive Testing Conference and Exhibition, Nov. 27-30, 2005, 14 pages.*

(Continued)

*Primary Examiner* — David Porta
*Assistant Examiner* — Mindy Vu
(74) *Attorney, Agent, or Firm* — Richard C Litman

(57) ABSTRACT

The systems for determining and imaging wax deposition and simultaneous corrosion and wax deposit determination in pipelines relate to systems for determining wax deposition and corrosion by one or both of two techniques. In both techniques, a source of neutron radiation is directed at the pipeline. In one technique, a neutron detector surrounded by an absorption shield defining a collimation window counts neutrons reflected back to the detector by back diffusion or backscatter radiation. In the other technique, a gamma ray detector measures gamma rays emitted when the emitted neutrons are absorbed in the pipeline. A neutron moderator-reflector is placed around three sides of the pipeline to increase the likelihood of neutron capture.

10 Claims, 7 Drawing Sheets

(56) References Cited

U.S. PATENT DOCUMENTS

| | | | |
|---|---|---|---|
| 5,687,606 | A | 11/1997 | Reilly |
| 5,970,116 | A | 10/1999 | Dueholm et al. |
| 6,252,930 | B1 | 6/2001 | MacKenzie |
| 6,421,418 | B1 | 7/2002 | Schulte |
| 6,895,074 | B2 | 5/2005 | Benedetti |
| 2006/0098773 | A1* | 5/2006 | Peschmann .................... 378/57 |
| 2010/0225477 | A1* | 9/2010 | Livchak et al. ............... 340/540 |

FOREIGN PATENT DOCUMENTS

| | | |
|---|---|---|
| KR | 10-2009-0070616 | 7/2009 |
| WO | WO 9733141 A1 | 9/1997 |
| WO | WO 9914581 A1 | 3/1999 |

OTHER PUBLICATIONS

Samir Abdul-Majid and Ahmed Balamesh, "Imaging Corrosion Under Insulation by Gamma Ray Backscattering Method", 18th World Conference on Nondestructive Testing, Apr. 16-20, 2012, Durban, South Africa.

Samir Abdul-Majid et al., "Use of Gamma Ray Back Scattering Method for Inspection of Corrosion under Insulation," 3rd MENDT—Middle East Testing Conference and Exhibition, Nov. 27-30, 2005, 8 pages, published online at www.ndt.net.

* cited by examiner

US 9,151,722 B2

SYSTEMS FOR DETERMINING AND IMAGING WAX DEPOSITION AND SIMULTANEOUS CORROSION AND WAX DEPOSIT DETERMINATION IN PIPELINES

CROSS-REFERENCE TO RELATED APPLICATION

This application claims the benefit of U.S. Provisional Patent Application Ser. No. 61/927,950, filed Jan. 15, 2014.

BACKGROUND OF THE INVENTION

1. Field of the Invention

The present invention relates to the determination of the extent of deposition of wax and/or corrosion in a pipeline, and particularly to a system for determining and imaging wax deposition and corrosion in a pipeline that uses a neutron source, neutron and/or gamma ray detectors, and backscatter diffusion collimation.

2. Description of the Related Art

Paraffin and asphalt deposition in crude oil transport is a very costly problem in oil industry. The accumulation of wax on the inner surface of pipes reduces flow and may cause a blockage in a pipeline that may stop oil production. Prediction of deposit thickness is very difficult due to the complex compositions of crude oil. At or below the Wax Appearance Temperature (WAT), hydrocarbon molecules crystallize and precipitate as solids. Hydrocarbons with more than 20 carbon atoms become solid at room temperature. Deposition is also a function of system pressure, composition and pipe inner surface properties. Wax deposition in pipelines can be very costly for plant operation in the oil industry. New techniques are needed for allocation and thickness determination of wax deposits. The timely removal of wax can produce large savings in the plant's operational cost.

Thus, systems for determining and imaging wax deposition and simultaneous corrosion and wax deposit determination in pipelines solving the aforementioned problems is desired.

SUMMARY OF THE INVENTION

The systems for determining and imaging wax deposition and simultaneous corrosion and wax deposit determination in pipelines relates to a system for determining wax deposition and corrosion by one or both of two techniques. In both techniques, a source of neutron radiation is directed at the pipeline. In one technique, a neutron detector surrounded by an absorption shield defining a collimation window counts neutrons reflected back to the detector by back diffusion or backscatter radiation. In the other technique, a gamma ray detector measures gamma rays emitted when the emitted neutrons are absorbed in the pipeline. A neutron moderator-reflector is placed around the pipeline to increase the likelihood of neutron capture.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The systems for determining and imaging wax deposition and simultaneous corrosion and wax deposit determination in pipelines relate to techniques in which a source of neutron radiation is directed at the pipeline. In a first technique, a neutron detector surrounded by an absorption shield defining a collimation window counts neutrons reflected back to the detector by back diffusion or backscatter radiation. In the other technique, a gamma ray detector measures gamma rays emitted when the emitted neutrons are absorbed in the pipeline. A neutron moderator-reflector like water is placed around three sides, e.g., top, left, and bottom portions of the pipeline to increase the likelihood of neutron capture. The system will be illustrated in the following examples.

Two types of hydrocarbon scale were investigated, namely, asphalt and paraffin wax, having specific gravities of 2.0 and 0.9, respectively. Actual organic scale is usually a mixture of these materials, and also contains small amounts of other molecules (such as molecules containing Fe, Ni, Cu, S, Ca, Si, O, etc.), depending on the location of the scale in the plant. In a real inspection, the measurement system needs to be calibrated for the scale type and the specific location. Carbon steel pipes of 16 cm and 10 cm diameters were used for the sample measurements described herein. These are medium-size pipes commonly used in most industrial plants.

The neutron sources used in this work were $^{241}$Am—Be and $^{252}$Cf. $^{241}$Am—Be has a half-life of 536 yr., and the activity of the material used here was approximately $1.11 \times 10^{11}$ Bq (3Ci), emitting $6.6 \times 10^6$ n/s with a tolerance of about ±10%. The bare source gave a neutron dose of approximately $6.6 \times 10^{-2}$ mSv/h and a gamma dose of $6.57 \times 10^{-2}$ mSv/h at 1 m distance, for a total of 0.12 mSv/h. $^{252}$Cf has a 2.64 yr. half-life and emits approximately $5 \times 10^7$ n/s (22 mg or 0.44GBq). A bare source gives a neutron dose of approximately 0.5 mSv/h and a gamma dose of 0.03 mSv/h, for a total of 0.53 mSv/h. The neutron spectrum of $^{252}$Cf is a fission spectrum with an average energy of 2.3 MeV, while the $^{241}$Am—Be has a harder spectrum with an average energy of 3.9 MeV.

The slow neutron detector was a $BF_3$ gas-filled proportional counter (LND Inc., model 202A, U.S.A). Because the neutron cross section for boron is much higher at slow neutron energy, a $BF_3$ detector exposed to neutrons will respond primarily to slow neutrons. The detector was used with the associated electronic components of a power supply (type2000 Canberra, Meriden Conn., U.S.A), a preamplifier (type 1406 Canberra, U.S.A), an amplifier (type 2012 Canberra, U.S.A) and an 8192 multi-channel analyzer (PC with special electronic card).

Figure 1A:
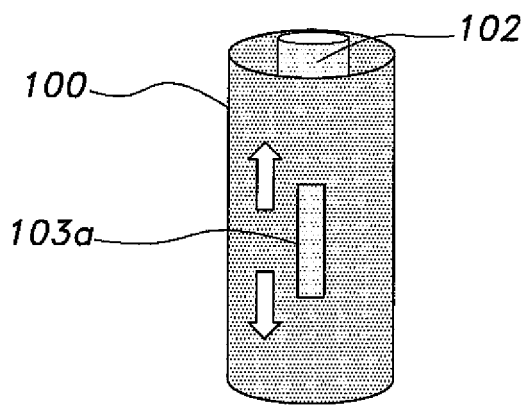
FIG. 1A is a diagrammatic perspective view of a first embodiment of a neutron detector for systems for determining and imaging wax deposition and simultaneous corrosion and wax deposit determination in pipelines according to the present invention, showing details of the detector's collimator.
Figure 1B:
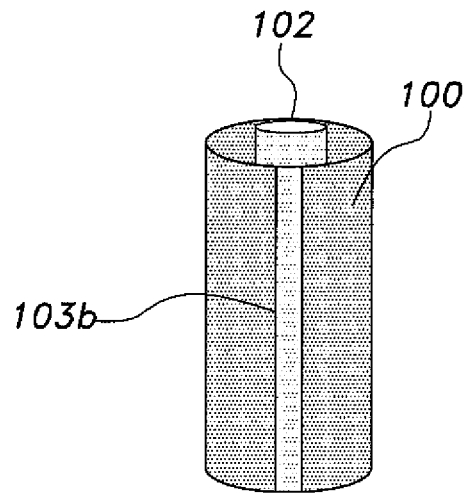
FIG. 1B is a diagrammatic perspective view of a second embodiment of a neutron detector for systems for determining and imaging wax deposition and simultaneous corrosion and wax deposit determination in pipelines according to the present invention, showing details of the detector's collimator.
Figure 1C:
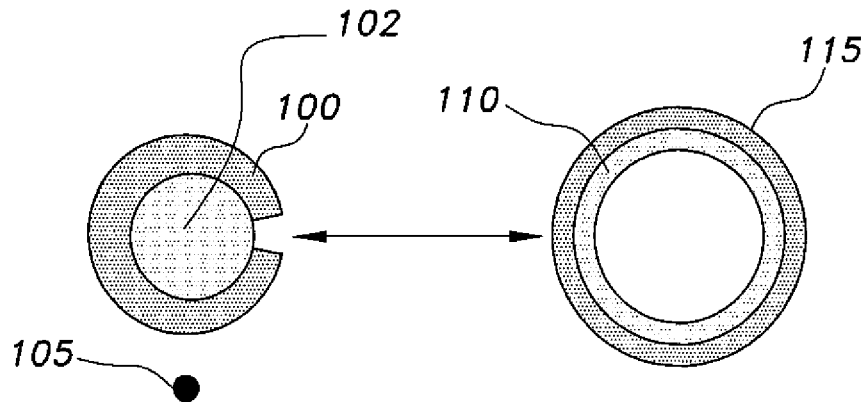
FIG. 1C is a diagrammatic environmental top view of a neutron detector for systems for determining and imaging wax deposition and simultaneous corrosion and wax deposit determination in pipelines according to the present invention, showing positioning of the neutron detector in relation to the pipe to be measured.

The experimental setup of the neutron back diffusion experiment is shown in FIGS. 1A-1C. As shown in FIGS. 1A and 1B, a cylindrical neutron absorber or shield 100 is disposed coaxially around a $BF_3$ neutron detector 102, and may either have a small, adjustable height collimator window 103a or an elongate collimator window 103b extending along the length of the shield 100. As shown in FIG. 1C, a radiation source 105 is disposed near the neutron absorber/detector 100, 102 and aimed at the pipeline 115 to be measured. The slit 103b or window 103a is aimed lengthwise at a section of the pipe 115 having an organic scale buildup 110. Fast neutrons emitted from the source 105 penetrate the iron pipe 115 without significant absorption because iron has a small absorption cross section for fast neutrons. Fast neutrons interact elastically with the hydrogen and carbon atoms of the organic scale 110 and are thereby slowed down. Some of the slowed-down neutrons will move backwards and are detected by the $BF_3$ neutron detector 102, the count rate of which increases with the amount of scale 110. A thicker scale 110 leads to more moderation and backscattering of the slow neutrons.

The $BF_3$ detector is surrounded with 2.5-cm-thick boron powder that functions as a shield 100 to stop slow neutrons coming directly from the source 105, or from unwanted neutron interaction with materials other than the sample, except for a 1-cm-wide window 103a facing the pipe 110. Different thicknesses of cadmium were also used around the detector 102 to stop slow neutrons, and no further reduction in background radiation levels was observed after approximately 1 mm thickness of cadmium. The background radiation with 5 mm boron reduced three-fold more than with Cd of approximately the same thickness. Cadmium stops almost all neutrons below the cut-off energy of approximately 0.4 eV. Neutrons from the scale with greater energy can penetrate Cd and produce counts in the $BF_3$ detector, particularly given that the boron cross section at this energy is not small (approximately 170 b).

Gamma rays with different levels of energy are emitted following the absorption of slow neutrons by detector materials, shields, and other materials. The counting system has been set to discriminate against these gamma rays. The slow neutrons are measured from the 2.31 MeV alpha particle peak.

Figure 2:
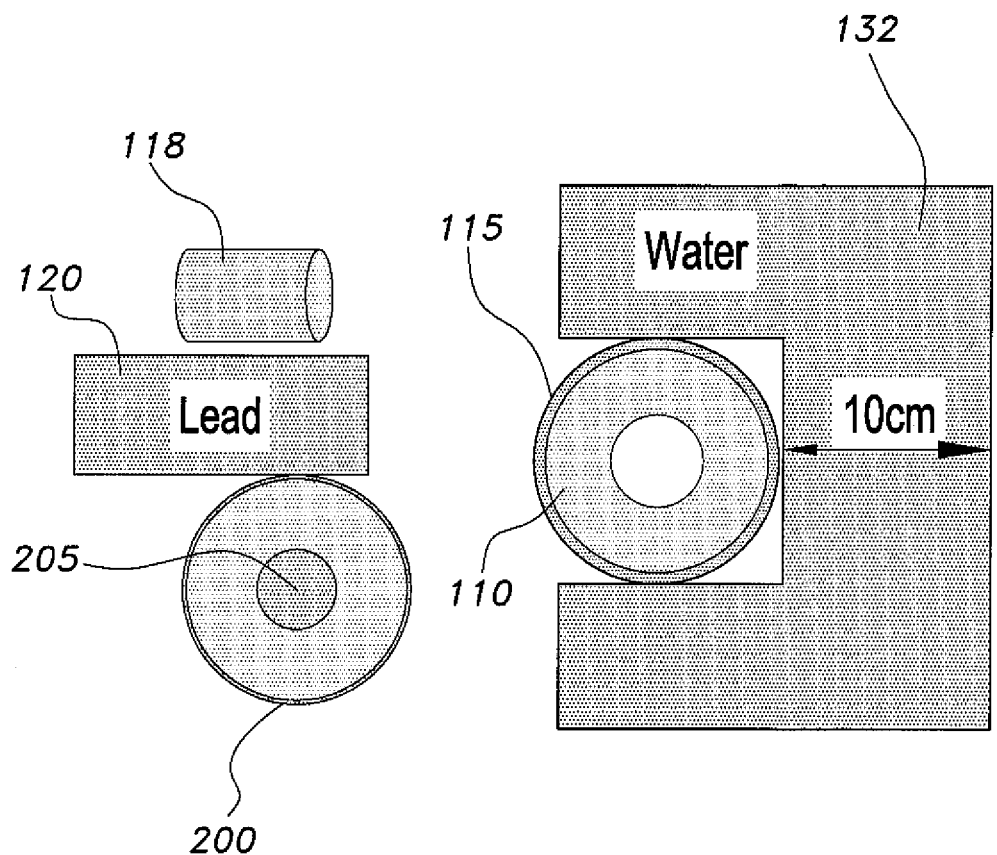
FIG. 2 is a schematic diagram of a systems for determining and imaging wax deposition and simultaneous corrosion and wax deposit determination in pipelines according to the present invention, showing the system configured for detecting gamma rays emitted upon neutron capture.

The experimental arrangement of the neutron capture gamma ray method is shown in FIG. 2. The same neutron sources (shown in FIG. 2 as 205) were used together with a high purity germanium detector (HPGe) 118, multichannel analyzer and associated nuclear electronics components. A 10-cm-thick layer of paraffin 200 surrounds the source 205 and a 10-cm-thick layer of water is place in a vessel such as, for example, U shaped tube 132 that surrounds the pipe 115, as shown in FIG. 2, to moderate fast neutrons, increasing the probability of neutron capture at the pipe position. It should be understood that the 10 cm thickness dimension of the tube 132 is exemplary only and that other dimensions commensurate with the dimensional scale of the pipe are contemplated by the present invention. Similarly, lead blocks 120 are an exemplary ten centimeters thick and are placed between the source 205 and the detector 118 to stop gamma rays coming directly from the source 205 and the paraffin moderator 200. Lead blocks 120 are exemplary and it should be understood that other gamma shields such as, for example without limitation, tungsten may be used. Lead may also be placed underneath the setup to stop the capture of gamma rays coming from the concrete floor. Water in concrete contains hydrogen atoms that would emit gamma rays that interfere with the signal to be measured from the hydrogen atoms of the organic scale. The energy of the system can be calibrated using several known sources, such as $^{137}$Cs (0.662 MeV), 60Co (1.332 MeV and 1.17 MeV) and neutron capture gamma rays of H (2.223 MeV), Fe (7.632 MeV) and C (4.945 MeV).

With respect to neutron back diffusion, plot 300 (shown in FIG. 3) represents the counts for two minutes of back diffused neutrons in the vertically positioned detector 102 surrounded by 2.5 cm boron 100 with a 1-cm wide window 103b along the detector 102 (see FIG. 1B). The average slope of the curve is 1880 counts/cm for a counting time of two minutes. The median standard deviation is approximately 40. If two counts that differ by 2 standard deviations can be distinguished, then a change in thickness of approximately 0.5 mm can be detected. The sensitivity can be significantly improved for longer counting times or using a stronger source.

Figure 3:
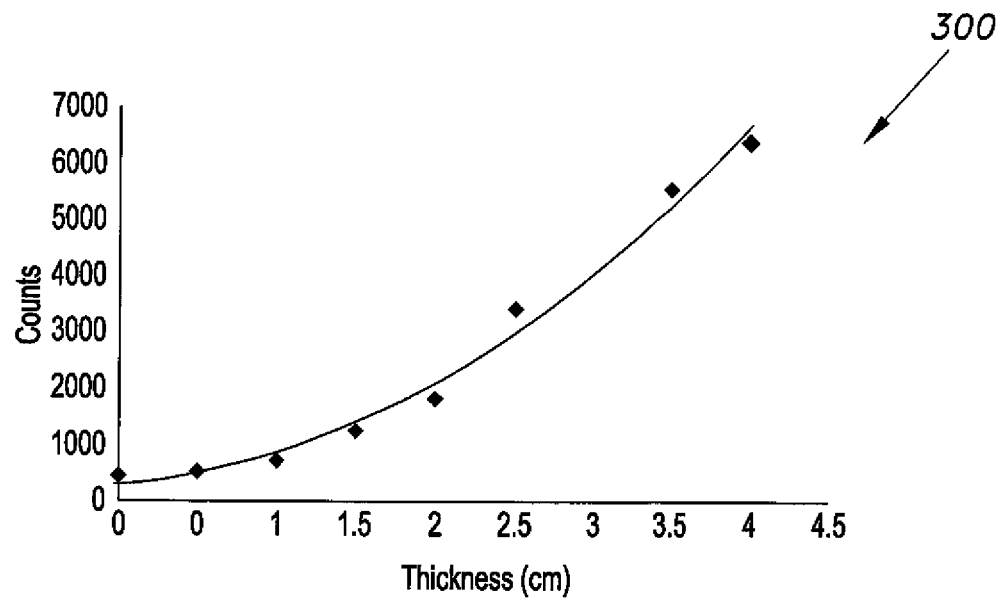
FIG. 3 is a plot showing counts for two minutes of back diffused neutrons as a function of the thickness of asphalt wax deposited inside a pipeline with a 1 cm wide collimator window along a vertically oriented neutron detector.
Figure 4:
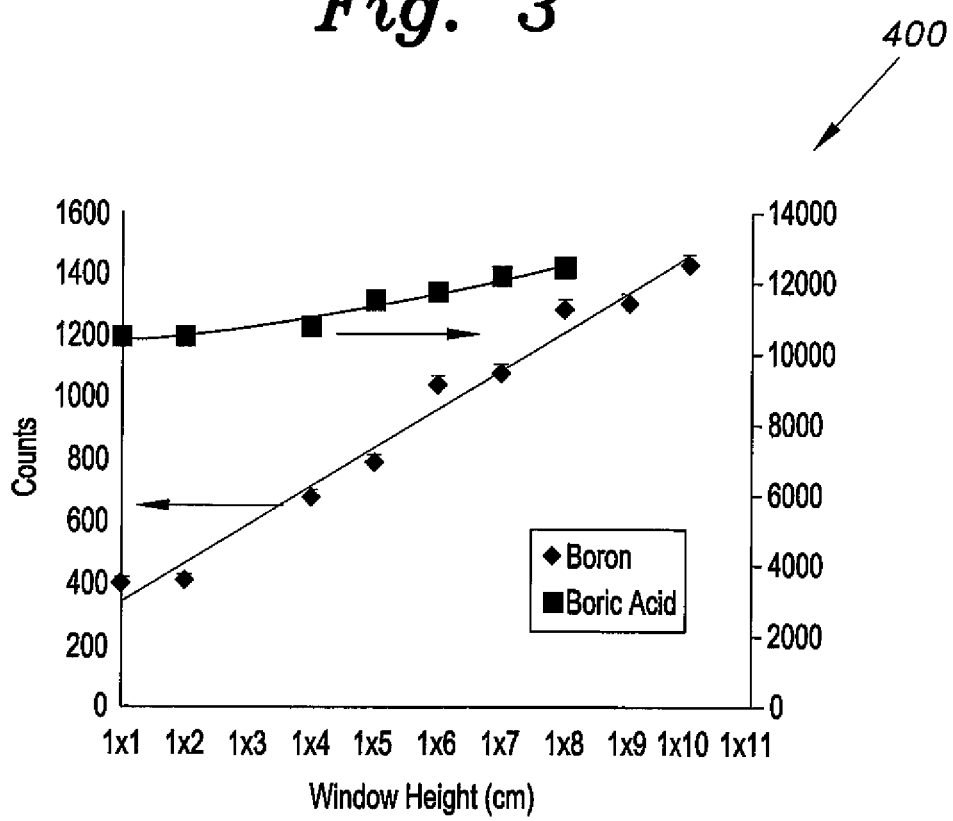
FIG. 4 is a plot showing counts for back diffused neutrons as a function of window height of the collimator along a vertically oriented neutron detector.

One important aspect of scale inspection is the distribution of the thickness inside the pipe. The measurement illustrated in plot 300 of FIG. 3 gives the average thickness along the detector. To study the detection in a smaller region, the detector window facing the pipe was gradually reduced using the adjustable height window 103a shown in FIG. 1A. Plot 400 of FIG. 4 shows counts from different window heights for an asphalt thickness of approximately 3 cm. Boric acid was also tested as an absorbing agent around the detector. Boric acid ($H_3BO_3$) is readily available and much less expensive than pure boron. The result in FIG. 4 shows that boric acid absorbed fewer neutrons coming directly from the source 105, compared with the same thickness of pure boron, and gave a much higher background. Boric acid has a lower atomic concentration of boron and a lower specific gravity of 1.435 compared with 2.08. However, because of its low cost, it might be considered for applications where high accuracy is not critical.

Figure 5:
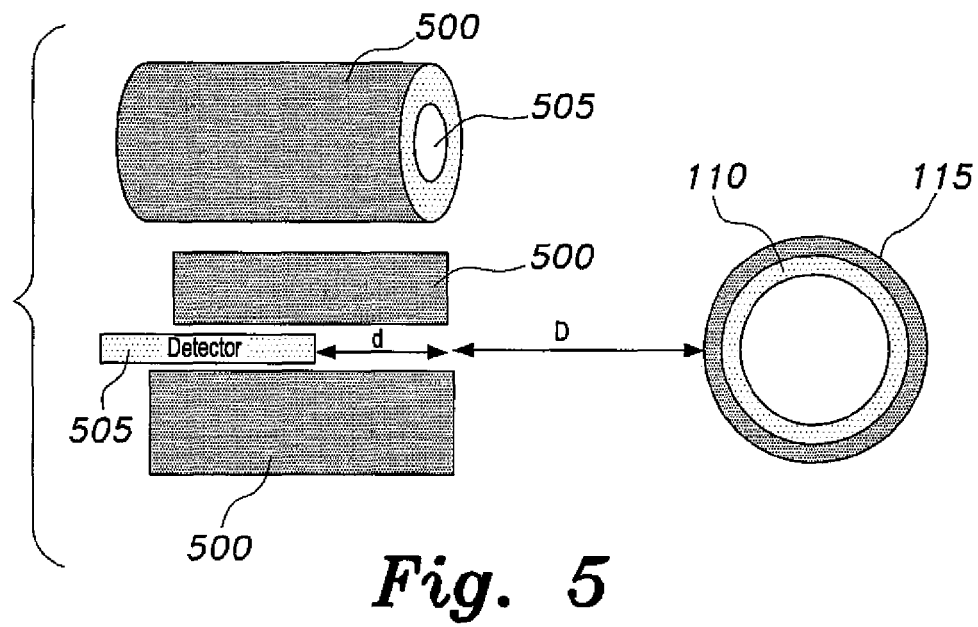
FIG. 5 is a schematic diagram of an alternative embodiment of a systems for determining and imaging wax deposition and simultaneous corrosion and wax deposit determination in pipelines according to the present invention having a horizontally oriented neutron detector.

Another arrangement for the collimation of back diffused neutrons was tested, as shown in FIG. 5. The detector 505 was covered with a 2.5-cm thick layer of boron and laid horizontally, and an opening of 2 cm in diameter was made at the base of the cylindrical absorber 500 for detector insertion.

Figure 6:
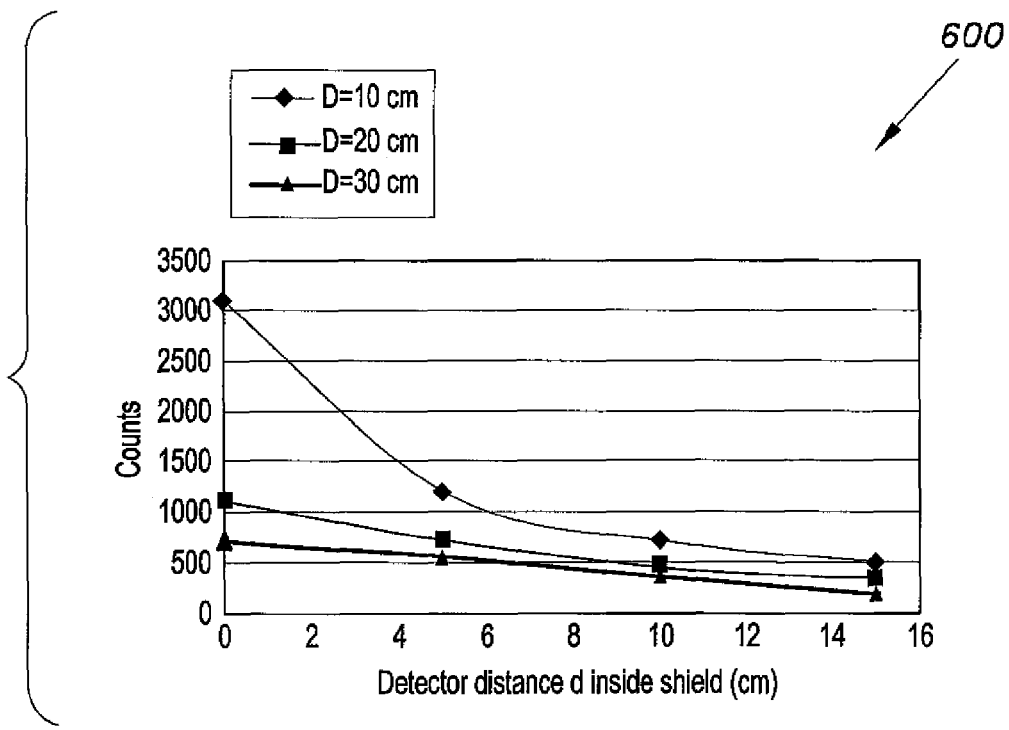
FIG. 6 is a plot showing counts for two minutes of paraffin back diffused neutrons as a function of detector distance d inside the shield for the horizontally oriented neutron detector of FIG. 5.
Figure 7:
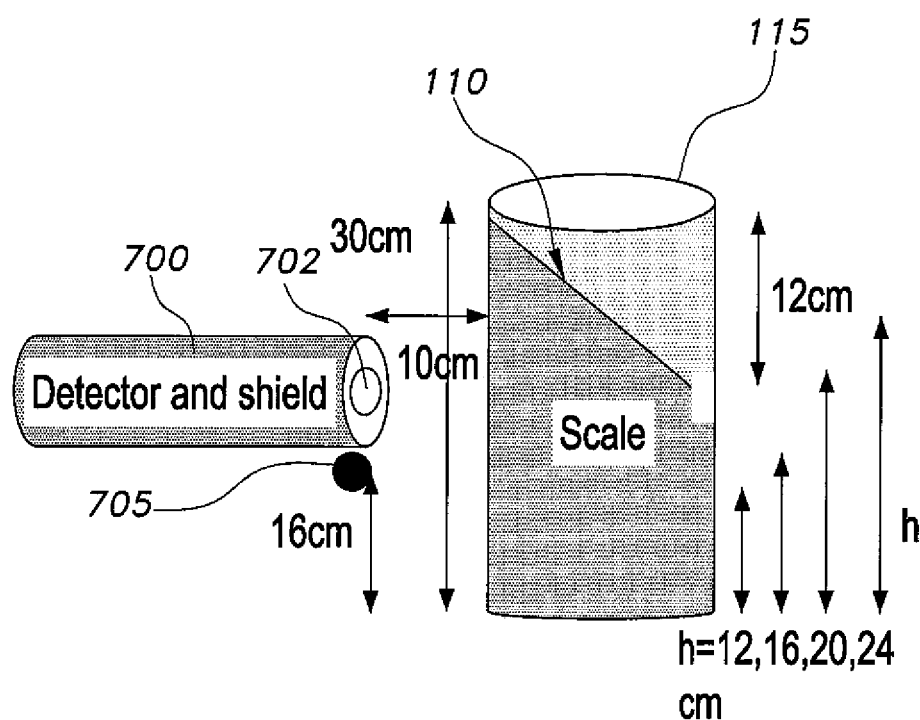
FIG. 7 is a schematic drawing showing the system of FIG. 5 configured for vertical scanning of a vertically oriented pipe having increased thickness of scale (paraffin scale) from top to bottom of the pipe.
Figure 8:
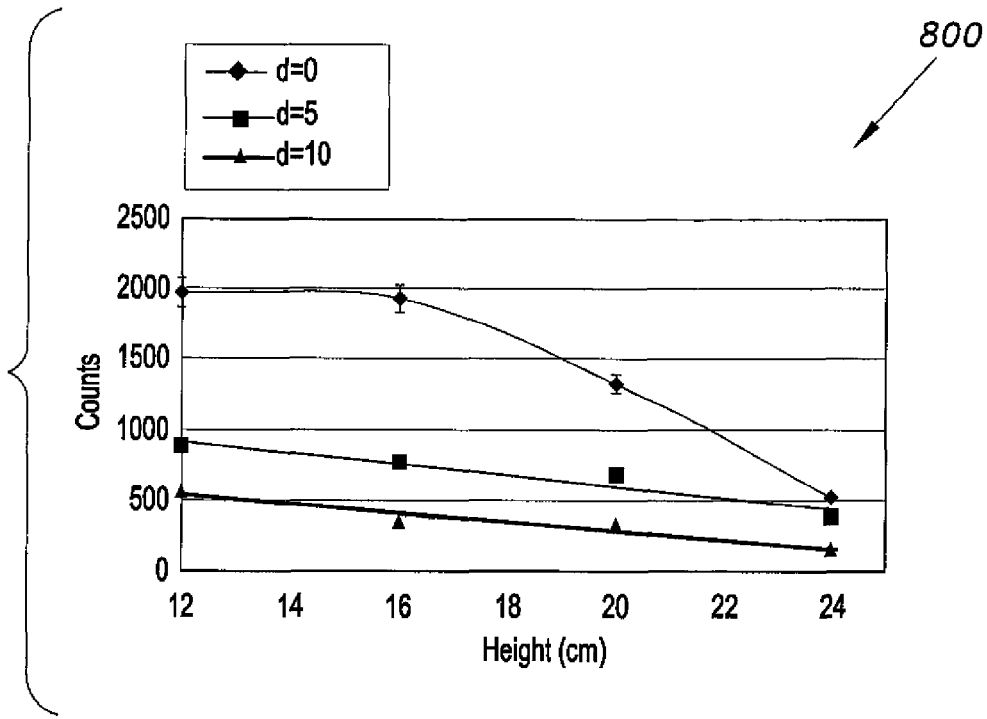
FIG. 8 is a plot showing counts of back diffused neutrons from paraffin as a function of detector height and detector distance inside the shield using the system of FIG. 7.

The collimation was studied by varying the distance D between the absorber 500 and the pipe 115 and varying the distance d of the detector 505 from the edge of absorber 500. The results, shown in plot 600 of FIG. 6, demonstrate that collimation improved as both distances were increased. Increasing either distance provides a better shield and allows the detector to see a smaller region of pipe and scale. At a distance d of approximately 5 cm (between the detector 505 and the edge of the absorber 500), the counts are near saturation at all distances D between the shield and pipe. At this value, the detector response to a region from the pipe 115 is almost equal to the opening window at the base of the absorber 500. Measurements of paraffin scale of varying thickness were performed using the experimental setup shown in FIG. 7. The absorber 700, the detector 702 and the source 705 were configured for vertical scanning. The thickness of paraffin scale 110 increased from zero at the top of the pipe 115 to almost filling the pipe 115 at a height of 18 cm from the bottom. Counts at different detector heights from the bottom of the pipe 115 are shown in plot 800 of FIG. 8. When the detector 702 was at the face of the absorber 700 (d=0), no significant difference in counts of back diffused neutrons was observed at heights of 12 and 16 cm because the detector 702 saw all scale thicknesses. As the detector height was raised, the scale thickness decreased gradually and fewer back diffused neutrons were detected. Between h=16 and h=24 the counts decreased almost linearly. Placing the detector 702 at distances 5 cm and 10 cm inside the shield 700 yielded better collimation at the expense of total counts. Additionally, as the distance between the pipe 115 and the detector 702 increased, fewer counts were detected for thicker samples.

Figure 9:
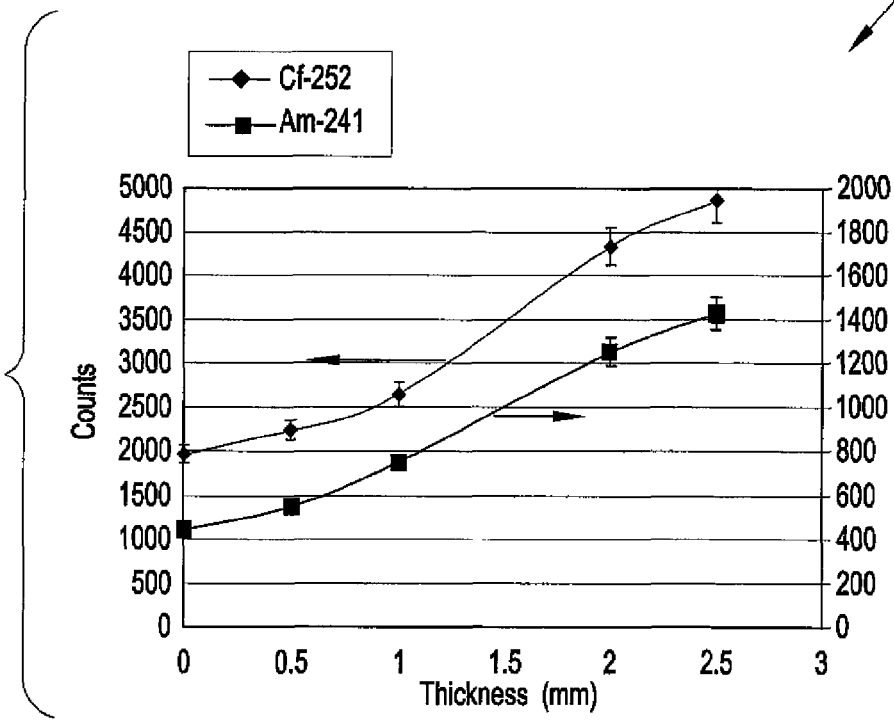
FIG. 9 is a plot showing counts of back diffused neutrons from polyethylene films as a function of the thickness of the polyethylene films using different sources of neutron radiation.

The system sensitivity of collimated back diffused neutrons to a change in polyethylene thickness, (in the form of thin sheets) can be obtained with reference to plot 900 of FIG. 9. This setup is similar to that shown in FIG. 5, except that the detector was at the face of the shield (d=0) and the distance between the shield and pipe D was 2 cm. Counts were collected for 10 min using both $^{252}Cf$ and $^{241}Am$. The average slope in the middle of the curve is 1600 counts/mm for ten minutes counting time (2.7 $mm^{-1}$ $s^{-1}$), and the standard deviation is approximately 40, so that a change in thickness of less than one mm in can be detected. The sensitivity for $^{252}Cf$ is $0.54 \times 10^{-7}$ $mm^{-1}$ per unit neutron strength (2.7 $mm^{-1}$ $s^{-1}$/ $5 \times 10^7$ n $s^{-1}$). The sensitivity with a ten minute counting time is quite practical for real inspections. The sensitivity can be improved by using a long counting time or a stronger source.

One important application of neutron capture gamma ray is the simultaneous measurement of the thicknesses of the iron wall and scale. Wall thickness may reduce with time due to corrosion or erosion.

Figure 10:
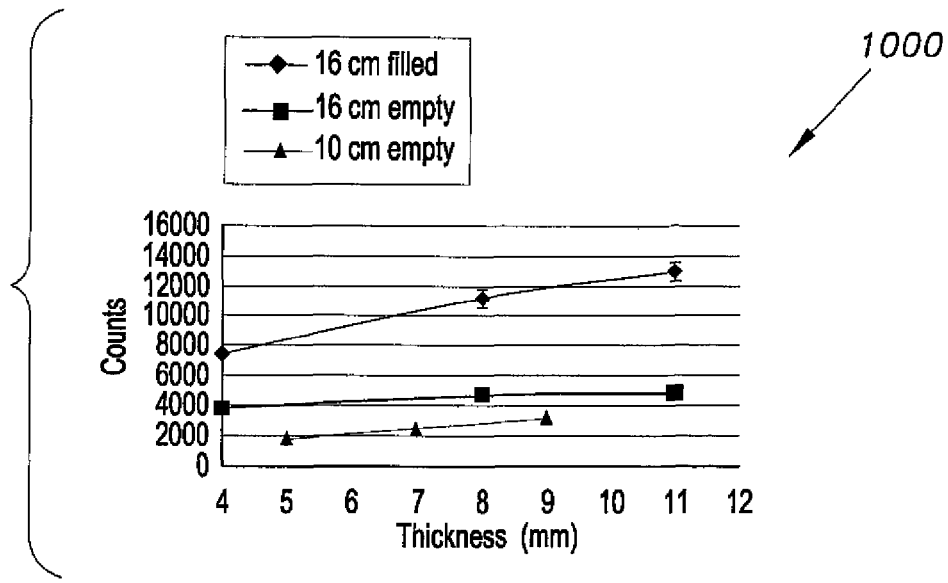
FIG. 10 is a plot showing gamma counts for one hour of the 7.63 MeV gamma ray iron double escape peak for 10 cm and 16 cm pipes as a function of wall thickness measured with the system of FIG. 2.

Plot 1000 of FIG. 10 shows gamma counts for one hour of detection of an iron 7.63 MeV gamma ray double escape peak using an HPGe (high purity germanium) detector and a $^{241}Am$—Be source as a function of the wall thickness of the iron pipe for two pipe sizes of 10 and 16 cm, using the setup shown in FIG. 2. The larger diameter pipe produces higher counts because more material is available for interaction. For the 16 cm diameter pipe, measurements were made when the pipe was empty and when it was filled with water. The water-filled pipe gave higher counts because the water further slows down the neutrons. Counts had an almost linear relationship with wall thickness. Counts are expected to saturate at much higher iron thicknesses because of the self-absorption of both incident neutrons and gamma rays emitted from iron. In such industries as petrochemical or desalination plants, the liquid inside the pipe can be ordinary water, saline water, or organic liquid. These liquids can have slight differences in the moderating ratio. Also, in two-phase flow, the pipe is neither empty nor filled with water. Calibration will be needed at the actual ratio. If this ratio changes significantly, then it is better to make measurement when no flow is in the pipe.

Using the same setup, the 7.63 MeV emitted from iron and the 2.23 MeV emitted from the hydrogen in the organic scale were measured at the same time as a function of asphalt scale thickness. The results are shown in plot 1100 of FIG. 11. Practical applications require the collection of a set of curves similar to those shown in this figure at different pipe wall and asphalt thicknesses.

Few studies have been reported in the literature on measurements of organic scale in pipes or vessels, despite the importance of scale accumulation for many industries. A successful online system can save money by reducing the frequency of plant shutdowns and the unnecessary replacement of components that may still have functional life remaining.

The method described here can work from one side of the object, and therefore is feasible for scale inspection of large vessels, having very large pipes or pipes where only one side can be accessed. The method is also non-contact, and can work on very hot pipes or tanks.

The neutron back diffusion method developed herein is rapid and sensitive. As shown in FIG. 3, two minutes of counting was adequate to provide reliable results. A fraction of a millimeter change in scale thickness can be detected in a very short counting time. The system components are inexpensive, and the weight of all the components is less than 1 kg.

Although the $BF_3$ detector was quite useful for these measurements, higher efficiency and smaller diameter detectors can be found that may provide higher accuracy and efficiency. The pipes used in this work are medium-sized pipes. Calibration will be needed to enable inspection of pipes of other sizes.

The boron shield provided better background reduction than the expensive Cd metal. Boric acid is much cheaper than B or Cd, and can be used for neutron absorption if high accuracy is not needed.

Additionally, a detector without an absorber provides both a higher signal and higher background counts. This may be useful for conducting a fast survey of scale. A bare detector would respond to other nearby materials, such as plastic, wood, moisture, and concrete.

Scale distribution measurements can provide useful information on scale accumulation behavior and on the performance of plant components. The horizontally positioned detector with collimation from the shield base provided more useful information (see FIG. 5 and FIG. 7) than the vertically positioned detector (FIG. 3).). Scale can be measured from within a small portion of the pipe. The reduction in counting sensitivity can always be compensated by extending the counting time.

Figure 11:
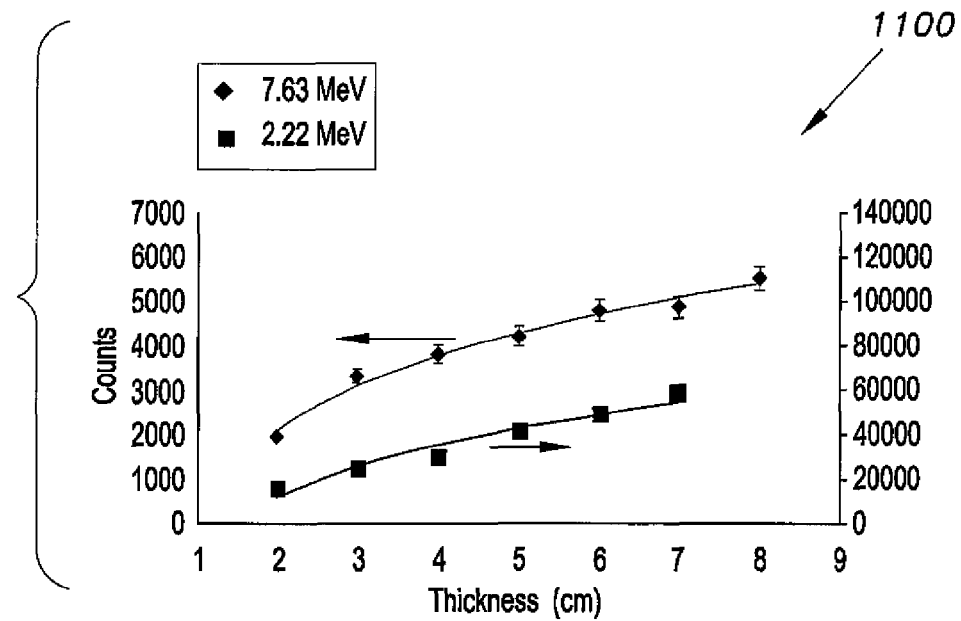
FIG. 11 is a plot showing simultaneous measurements for 1 hour of the net gamma counts of the 7.63 MeV iron single escape peak and the 2.23 MeV hydrogen peak for a 16 cm diameter pipe with 4 mm wall thickness as a function of paraffin scale thickness using the system of FIG. 2.

It should be clarified herein that if the system is to be used for online inspection, the flow of organic fluid needs to be stopped so that signals from the fluid do not interfere with signals from the scale. The main advantage of neutron capture gamma-ray over neutron back diffusion is that it provides simultaneous information on both the scale thickness and the corrosion or thickness of the pipe wall (FIG. 10 & FIG. 11). Portable HPGe detectors and multichannel analyzers are commercially available for field work, but this equipment is expensive and the setup is more complicated compared to the setup for neutron back diffusion.

Paraffin was used as the neutron moderator around the source in the neutron capture method. While polyethylene, for example, has a higher moderating ratio than paraffin and a higher melting point and is more practical for field work, it is much more expensive. This consideration also applies to the choice of water as a neutron moderator and reflector around the pipe. The moderator thicknesses were selected based on an optimization of the geometrical setup, although there might be some room for further improvements in geometry.

Many radioactive neutron sources can be used. The two sources studied here can achieve the goals of this work. The $^{252}$Cf source has a relatively short half-life of 2.64 y, so that frequent correction or calibration will be needed. This source also gives less radiation dose per unit strength than $^{241}$Am—Be. Higher activity sources can be used for more accurate or faster measurements. Neutron sources with a much higher activity are used for field applications, such as oil well logging. In industrial gamma radiography, sources of approximately 100 Ci $^{192}$Ir are used, and they are bare during imaging.

Such a source gives a dose of 420 mSv/h at 1 m, much higher than the dose given by the neutron sources used here of less than 1 mSv/h. A shield with source remote control can also significantly reduce the dose in all field applications.

It is to be understood that the present invention is not limited to the embodiments described above, but encompasses any and all embodiments within the scope of the following claims.

I claim:

1. A system for determination of wax deposition and corrosion in a pipeline, comprising:
    a neutron radiation source for emitting neutrons towards a pipeline;
    a slow neutron detector;
    an absorption shield having a high slow neutron absorption cross section surrounding the slow neutron detector, the absorption shield defining a collimation window for collimating neutrons diffusing back to the detector from the pipeline;
    wherein the absorption shield is cylindrical, collimation being adjustable by adjusting distance between the detector and the pipeline and by retracting the detector a selectable distance within the cylindrical absorption shield; and
    means for counting neutrons diffusing back to the slow neutron detector, the amount of wax deposition and corrosion in the pipeline being positively correlated with the count of neutrons as provided by the counting means.

2. The system for determination of wax deposition and corrosion in a pipeline according to claim 1, further comprising means for calibrating the system before the system is used to determine wax deposition and corrosion in the pipeline.

3. The system for determination of wax deposition and corrosion in a pipeline according to claim 1, wherein composition of the absorption shield surrounding the slow neutron detector is selected from the group consisting of a thick layer of boron powder, cadmium, and boric acid.

4. The system for determination of wax deposition and corrosion in a pipeline according to claim 1, wherein the absorption shield surrounding the slow neutron detector comprises a 2.5 cm thick layer of boron powder.

5. The system for determination of wax deposition and corrosion in a pipeline according to claim 1, wherein the counting means provides a proportional count of the neutrons detected at the slow neutron detector.

6. The system for determination of wax deposition and corrosion in a pipeline according to claim 1, wherein the collimation window aimed at the pipeline is 1 cm wide.

7. The system for determination of wax deposition and corrosion in a pipeline according to claim 1, wherein the collimation window is adjustable in height.

8. The system for determination of wax deposition and corrosion in a pipeline according to claim 1, wherein the detector is vertically oriented.

9. The system for determination of wax deposition and corrosion in a pipeline according to claim 1, wherein the neutron radiation source is selected from the group consisting of 241Am-Be and 252Cf.

10. The system for determination of wax deposition and corrosion in a pipeline according to claim 1, wherein the detector is oriented horizontally.

* * * * *